(12) United States Patent
Bakala et al.

(10) Patent No.: US 7,405,309 B2
(45) Date of Patent: Jul. 29, 2008

(54) PYRANONE DERIVATIVES USEFUL FOR TREATING CANCER

(75) Inventors: Joanna Bakala, Paris (FR); Denyse Herlem, Versailles (FR); Emile Benechie, Gif S/Yvette (FR); Jérôme Bignon, Le Val Saint Germain (FR); Françoise Khuong-Huu, Paris (FR); Pierre Potier, deceased, late of Paris (FR); by Guy Jean Marie Potier, legal representative, Paris (FR); by Marie-Claude Denise Michèle Zelveyan, legal representative, Asnieres (FR); by Catherine Marie Germaine Magnan, legal representative, Cabries (FR); by Odette Drion, legal representative, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 196 days.

(21) Appl. No.: 10/585,974

(22) PCT Filed: Jan. 14, 2005

(86) PCT No.: PCT/FR2005/000084

§ 371 (c)(1),
(2), (4) Date: Jul. 13, 2006

(87) PCT Pub. No.: WO2005/073211

PCT Pub. Date: Aug. 11, 2005

(65) Prior Publication Data

US 2007/0167515 A1  Jul. 19, 2007

(30) Foreign Application Priority Data

Jan. 14, 2004  (FR) ................................ 04 00298

(51) Int. Cl.
*C07D 309/38*  (2006.01)
*A61K 31/366*  (2006.01)
(52) U.S. Cl. ...................................... 549/294; 514/460
(58) Field of Classification Search ................. 549/294
See application file for complete search history.

(56) References Cited

U.S. PATENT DOCUMENTS 5,093,505 A   3/1992  Nishino et al.

*Primary Examiner*—D. Margaret Seaman
*Assistant Examiner*—Nizal S Chandrakumar
(74) *Attorney, Agent, or Firm*—Foley & Lardner LLP (57) ABSTRACT

The invention relates to pyranone derivatives of general formula (I), wherein X is chlorine, bromine or iodine and $R_1$ and $R_2$ is independently a hydrogen atom, an alkyl, cycloalkyl or alkylene, linear or branched group containing 1-20 carbon atoms, optionally substituted by a hydroxyl, amino, ether or halogen group, or $R_1$ and $R_2$ form together a cycle of 5, 6, 7 or 8 members which is optionally substituted by a hydroxyl, amino, ether or halogen group including isomers, enantiomers, diastereoisomers and the mixtures thereof. A method for preparing the inventive derivatives and the therapeutic use thereof, in particular for treating cancer, are also disclosed.

15 Claims, 4 Drawing Sheets

PYRANONE DERIVATIVES USEFUL FOR TREATING CANCER

This application is a National Stage application of PCT/FR2005/000084, filed Jan. 14, 2005, which claims priority from French patent application FR 0400298, filed Jan. 14, 2004. The entire contents of each of the aforementioned applications are incorporated herein by reference.

The subject of the present invention is pyranone derivatives of general formula (I), their method of preparation and their therapeutic application, in particular for the treatment of cancer. The subject of the present invention is also the intermediate compounds of general formula (IV).

Tumor diseases, which affect ten million people world wide, are, after cardiovascular diseases, the most deadly conditions. The efforts made during the past few years in various fields of research have led to a substantial improvement in cancer therapy. The advances in medical oncology are mainly due to the commercialization of novel cytotoxic medicaments (cisplatin, taxoids, irinotecam, topotecam and the like). Today, whether it is combined with radiotherapy or surgery or not, chemotherapy remains the predominant treatment in numerous cancers. Thus, the cytotoxic medicaments may be administered before a surgical operation or a radiotherapy in order to reduce the size of the tumor. They are also very often necessary after surgery or radiotherapy in order to remove all the cancer cells which may have been resistant to these treatments.

Yet, despite the regular introduction of novel medicaments, the chemotherapeutic approach in cancerology is reaching a plateau. Indeed, it has to be recognized that chemotherapy is a failure in the case of the most frequent solid tumors in western societies: breast, lung and prostate cancer, digestive and urinary tumors and the like. It often makes it possible to reduce the degree of seriousness of malignant tumors, but rarely leads to a cure.

One of the first objectives of the pharmacology of anticancer medicaments is therefore the constant search for novel drugs which are likely to show a better therapeutic efficacy. The first two criteria called into play in the selection of novel anticancer medicaments are:

1. the novelty of the chemical structure and of the mechanism of action,
2. the experimental antitumor activity in cellular models in vitro but in particular in animal models in vivo.

The applicant has thus found novel compounds derived from pyranone which exhibit all of these criteria.

The subject of the present invention is compounds of general formula (I)

in which

X represents chlorine, bromine or iodine, and $R_1$ and $R_2$ represent, each independently of the other, a hydrogen atom, an alkyl, cycloalkyl or alkylene group, which is linear or branched, advantageously linear, containing from 1 to 20 carbon atoms, optionally substituted with a hydroxyl, amino, ether or halogen group, or $R_1$ and $R_2$ form together a 5-, 6-, 7- or 8-membered ring, said ring being optionally substituted with a hydroxyl, amino, ether or halogen group, including its isomers, its enantiomers, its diastereoisomers, and mixtures thereof.

The compounds of formula (I) may contain one or more asymmetric carbon atoms when $R_1$ and $R_2$ are different from each other. They may therefore exist in the form of enantiomers or diastereoisomers. The compounds of formula (I) may also be provided in the form of cis or trans isomers. These isomers, enantiomers, diastereo-isomers and mixtures thereof, including the racemic mixtures, form part of the invention.

Advantageously, according to the present invention, $R_1$ and $R_2$ comprise from 1 to 15 carbon atoms, more advantageously still from 1 to 10 carbon atoms, more advantageously still from 1 to 5 carbon atoms.

In a specific embodiment according to the present invention, $R_1$ and $R_2$ form together a 5-, 6-, 7- or 8-membered ring, the ring being advantageously a saturated hydrocarbon ring. In a preferred specific embodiment according to the invention, $R_1$ and $R_2$ form together a 5- or 6-membered saturated hydrocarbon ring.

In the context of the present invention, the expression alkyl group is understood to mean a linear or branched saturated aliphatic group; there may be mentioned in particular methyl, ethyl, propyl, isopropyl, butyl, isobutyl, tert-butyl and pentyl groups, and the like, cycloalkyl group is understood to mean a cyclic alkyl group; there may be mentioned in particular cyclopropyl, cyclobutyl, cyclopentyl and cyclohexyl groups, and the like, halogen group is understood to mean fluorine, chlorine, bromine or iodine, alkylene group is understood to mean a linear or branched mono- or polyunsaturated aliphatic group preferably comprising one or two ethylenic saturations, amino group is understood to mean an $NH_2$ group or a secondary or tertiary amine group, an ether group is understood to mean an OR' group, R' being an alkyl radical such as methyl, ethyl, propyl, isopropyl, butyl, isobutyl, tert-butyl, pentyl and the like.

Among the compounds of formula (I) which are the subject of the present invention, there may be mentioned the preferred compounds which are defined as follows: X represents chlorine, bromine or iodine, and $R_1$ and $R_2$ each represent independently of each other a hydrogen atom, an alkyl or alkylene group, which is linear or branched, advantageously linear, containing from 1 to 20 carbon atoms, optionally substituted with an ether or halogen group, or $R_1$ and $R_2$ form together a 5-, 6-, 7- or 8-membered ring, said ring being optionally substituted with an ether or halogen group.

Among the latter preferred compounds, the compounds of formula (I) for which X represents iodine are most particularly preferred.

Among the latter preferred compounds, the compounds of formula (I) for which $R_1$ and $R_2$ each represent independently of each other a hydrogen atom, a methyl, ethyl, propyl or butyl group, are most particularly preferred.

Advantageously, according to the present invention, $R_1$ and $R_2$ each represent a methyl group or one of these two radicals represents a methyl group and the other represents a hydrogen atom.

Advantageously, according to the present invention, X represents iodine and $R_1$ and $R_2$ each represent a methyl group or one of these two radicals represents a methyl group and the other represents a hydrogen atom.

Among the latter preferred compounds, the compounds of formula (I) which are iodomethylene-dimethyl-dihydropyranones, for which X represents iodine and $R_1$ and $R_2$ each represent a methyl group, are most particularly preferred.

More advantageously still, according to the present invention, the compound of formula (I) is the isomer E-iodomethylene-dimethyl-dihydropyranone.

The subject of the present invention is also a method for preparing the compounds of general formula (I), in which a Horner-Emmons reaction is first carried out by reacting an aldehyde of formula (IV)

IV in which the meanings of X, $R_1$ and $R_2$ are those defined above for the compounds of formula (I), with a phosphonate such as methyl [bis(2,2,2-trifluoro-ethyl)phosphinoyl]acetate, and then a cyclization (lactonization) is carried out. Other phosphonates such as methyl [bis(2,4-difluorophenyl)phosphinoyl]acetate, methyl diphenyl-phosphinoyl-acetate, or the cyclic ethyl phosphinoyl-acetates derived from N,N'-dimethylethylenediamine described by: Carl Patois and Philippe Savignac Tetrahedron lett., 1991, 32, 1317-1320, may be used in the context of the present invention.

Advantageously, according to the present invention, the preparation of the compound of formula (I) from the compound of formula (IV) is carried out in the presence of a base, advantageously a weak base, such as potassium carbonate and a crown ether such as the crown ether 18-crown-6. Other bases such as $KN(TMS)_2$, Triton B, NaH, LDA or 2,2,6,6-tetramethylpiperidine may be used in the context of the present invention. The presence of the crown ether makes it possible to complex the cation formed, combined with the base, and to thereby promote the production of an olefin having a z configuration required for the lactonization. This step, which consists in passing from the compound of formula (IV) to the compound of formula (I), is preferably carried out in a toluene type anhydrous solvent, under an inert atmosphere.

The compounds of general formula (I) may thus be synthesized according to the following scheme 1:

In a specific embodiment of the present invention, the preparation of the compound of formula (I) from the compound of formula (IV) is preceded by the following steps:

i) a compound of formula (II) is first of all reacted with a reducing agent such as lithium aluminum hydride, resulting in the formation of the corresponding primary alcohol (III), and then ii) the compound of formula (III) is reacted with an oxidizing agent such as manganese dioxide to give the corresponding aldehyde (IV)

in which the meanings of X, $R_1$ and $R_2$ are those defined above for the compounds of formula (I), and R represents a linear alkyl group containing from 1 to 5 carbon atoms, such as a methyl or ethyl group.

The compound (II) used according to the present invention is advantageously in the form of the cis (Z) isomer. The compound (II) may be synthesized from alkyl propiolate (HC≡C—CO$_2$R) and a ketone ($R_1COR_2$), R, $R_1$ and $R_2$ being defined as above, in the presence of tetrabutylammonium halide, an anhydrous solvent of the methylene chloride type and a Lewis acid such as zirconium tetrachloride or diethylaluminum iodide. The synthesis of the compound (II) is preferably carried out in the region of 0° C., under an inert atmosphere.

Step (i) of the method according to the present invention, which consists in reducing the ester functional group of the compound (II), resulting in the formation of the corresponding primary alcohol (III), is carried out with the aid of a reducing agent such as lithium aluminum hydride, lithium borohydride or diisobutylaluminum hydride. This step (i) is preferably carried out in an anhydrous solvent of the ether type, under an inert atmosphere, at room temperature.

Step (ii) of the method according to the present invention, which consists in oxidizing the primary alcohol functional group of the compound (III), resulting in the formation of the corresponding aldehyde (IV), is carried out with the aid of an oxidizing agent such as manganese dioxide or Dess-Martin periodinane. This step (ii) is preferably carried out in an anhydrous solvent of the methylene chloride type, under an inert atmosphere, at room temperature.

In a specific embodiment of the present invention, when the radicals $R_1$ and $R_2$ of the compounds of general formula (I) are substituted with hydroxyl or amino type groups, said groups are protected throughout the synthesis for passing from the compounds of formula (II) to the compounds of formula (III) and then (IV), and from the compounds of formula (IV) to the compounds of formula (I) with protecting groups.

The expression protecting group is understood to mean, for the purposes of the present invention, a group which makes it possible, on the one hand, to protect a reactive functional group such as a hydroxyl or an amine during a synthesis and, on the other hand, to regenerate the intact reactive functional group at the end of the synthesis. Examples of protecting groups and the methods of protection and deprotection are described in Protective groups in Organics Synthesis, Green et al., $2^{nd}$ Ed. (John Wiley & Sons, Inc., New York).

The subject of the present invention is also the intermediate compounds of general formula (IV)

IV in which the meanings of X, $R_1$ and $R_2$ are those defined above for the compounds of formula (I), including its isomers, its enantiomers, its diastereoisomers and mixtures thereof.

The compounds of formula (IV) may contain one or more asymmetric carbon atoms when $R_1$ and $R_2$ are different from each other. They may therefore exist in the form of enantiomers or diastereoisomers. The corresponding compounds of formula (I) may exist predominantly in the form of cis or trans isomers, advantageously in the form of trans isomers, in particular when neither $R_1$ nor $R_2$ represents the hydrogen atom. The compounds of formula (I) may also be provided in the form of a mixture of cis and trans isomers, in particular when $R_1$ or $R_2$ represents the hydrogen atom. These isomers, enantiomers and diastereoisomers, and mixtures thereof, including the racemic mixtures, form part of the invention.

Advantageously, according to the present invention, the radicals $R_1$ and $R_2$ of the compounds (IV) comprise from 1 to 15 carbon atoms, more advantageously still from 1 to 10 carbon atoms, more advantageously still from 1 to 5 carbon atoms.

Among the compounds of formula (IV) which are the subject of the present invention, there may be mentioned the preferred compounds which are defined as follows: X represents iodine.

Advantageously, according to the present invention, $R_1$ and $R_2$ each represent a methyl group or one of these two radicals represents a methyl group and the other represents a hydrogen atom.

Advantageously, according to the present invention, X represents iodine and $R_1$ and $R_2$ each represent a methyl group or one of these two radicals represents a methyl group and the other represents a hydrogen atom.

Among the latter preferred compounds, the compounds of formula (IV), for which X represents iodine and $R_1$ and $R_2$ each represent a methyl group, are most particularly preferred.

The compounds (I) of the invention have been the subject of pharmacological trials which make it possible to determine their antitumor activity and their cytotoxic activity on cancer cell lines.

1. Trials consisted in measuring the cytotoxic activity in vitro of the compounds of the invention on cancer cell lines of different tissue origins (leukemia, breast, colon and mouth cancer), and on chemoresistant cells.

It thus appears that the compounds (I) of the invention block the division of tumor cells in the G2M phase of the cell cycle and cause the death of these cells by apoptosis.

2. Other trials consisting in measuring the antitumor activity in vivo of the compounds (I) of the invention have been carried out.

This antitumor activity of the compounds of the invention was studied on transplanted tumors (such as HCT-116) in Nude mice (nu/nu mice). Nude mice are immunodeficient mice having no thymus.

It therefore appears that the compounds (I) of the invention have antitumor activity, and can therefore be used for the preparation of medicaments having antitumor activity and cytotoxic activity on cancer cell lines. These medicaments find use in therapy, in particular in the treatment of cancer.

Thus, one of the subjects of the present invention is a medicament consisting of a compound of the invention of formula (I).

According to another of its aspects, the present invention relates to pharmaceutical compositions comprising, as active ingredient, a compound (I) according to the invention. Thus, these pharmaceutical compositions contain an effective dose of a compound (I) according to the invention, with any appropriate excipient, in particular one or more pharmaceutically acceptable excipient(s). Said excipients are chosen according to the pharmaceutical dosage form and the desired mode of administration.

The pharmaceutical compositions according to the present invention are advantageously intended to be administered by intravenous injection. The pharmaceutical compositions according to the present invention may also be administered by the following routes of administration: oral, sublingual, subcutaneous, intramuscular, topical, intratracheal, intranasal, transdermal or rectal route.

The active ingredient of formula (I) above may be administered in a unit form for administration, mixed with conventional pharmaceutical excipients, for the treatment of cancer. The appropriate unit forms for administration comprise the forms for oral administration, such as tablets, capsules, powders, granules and oral solutions or suspensions, the forms for sublingual, oral, intratracheal or intranasal administration, the forms for subcutaneous, intramuscular or intravenous administration and the forms for rectal administration. For topical application, it is possible to use the compounds according to the invention in creams, ointments or lotions.

When a solid composition in the form of tablets is prepared, the main active ingredient is mixed with a pharmaceutical excipient, such as gelatin, starch, lactose, magnesium stearate, talc, gum arabic and the like. The tablets may be coated with sucrose, a cellulose derivative or other materials. The tablets may be made by various techniques, direct tableting, dry granulation, wet granulation or hot-melt.

A preparation in the form of capsules is obtained by mixing the active ingredient with a diluent and pouring the mixture obtained into soft or hard capsules.

For parenteral administration, it is possible to use aqueous suspensions, isotonic saline solutions or sterile and injectable solutions which contain pharmacologically compatible dispersing agents and/or wetting agents, for example propylene glycol or butylene glycol.

The present invention, according to another of its aspects, also relates to the use of a compound of formula (I) according to the invention for the preparation of a medicament intended for treating cancer.

The following examples illustrate the present invention.

EXAMPLE 1

Preparation of Compounds of Formula (I): E-5-iodomethylene-6,6-dimethyl-5,6-dihydropyran-2-one X=I, R$_1$=CH$_3$, and R$_2$=CH$_3$ The synthesis of (I) was carried out from ethyl Z-2-(1-hydroxy-1-methylethyl)-3-iodoacrylate (II) according to the methods described respectively by Villieras et al. (Taïcir Ben Ayed, Jean Villieras, Hassan Ari, Tetrahedron, 2000, 56, 805-809) or by P. W. Pare et al. (Han-Xun Wei, Joe J. Gao, Guigen Li, Paul W. Paré, Tetrahedron Lett., 2002, 43, 5677-5680). The reduction of the ester functional group (II) with lithium aluminum hydride gives the primary alcohol (III). The oxidation of the primary alcohol functional group with manganese dioxide or with Dess-Martin periodinane gives the aldehyde (IV). The coupling of (IV) with methyl [bis(2,2,2-trifluoroethyl)phosphinoyl]acetate using potassium carbonate as base in the presence of the crown ether 18-crown-6 leads to the desired vinyl iodide (I) with a yield of 50% from the compound (II) (scheme 2)

Scheme 2

Scheme 2 reaction conditions: a-LAH, 1 eq., ether, room temperature (rt), 1 h, 75%; b-MnO$_2$, 10 eq., room temperature, CH$_2$Cl$_2$, 3 h, 90%; c-K$_2$CO$_3$, 6 eq., 18-crown-6/CH$_3$CN, 12 eq., toluene, 25° C., 1 h, then −20° C., (IV) 1 eq. and (CF$_3$CH$_2$O)$_2$P(O)—CH$_2$CO$_2$Me, 1 eq., −20° C. to 0° C., then 30 min at 0° C., 74%.

1.1. Preparation of Compounds of Formula (II): ethyl Z-2-(1-hydroxy-1-methylethyl)-3-iodoacrylate To a mixture of ethyl propiolate (19.3 mmol, 1.9 g or 1.96 ml), acetone redistilled over calcium sulfate (24 mmol, 1.76 ml) and tetrabutylammonium iodide (21.6 mmol, 8 g) in solution in 100 ml of anhydrous methylene chloride under an inert atmosphere (argon), zirconium tetrachloride (24 mmol, 5.6 g) is added at 0° C. The solution is stirred at 0° C. under argon for 5 h. After addition of water (20 ml), the organic products are extracted with methylene chloride (3 times 50 ml). The dried organic phases (MgSO$_4$) are evaporated under reduced pressure to give a residue (8.3 g) which is chromatographed on silica gel 60H Merck. By eluting with a CH$_2$Cl$_2$/MeOH mixture 98/2 then 97/3, the compound (II) (1.28 g, 23%) is obtained.

$^1$H NMR: δ ppm (CDCl$_3$, 250 MHz) 1.32 (3H, t, J=7.1 Hz, CH$_3$—CH$_2$), 1.39 (6H, s, (CH$_3$)$_2$—C), 2.83 (1H, s, OH), 4.27 (2H, q, J=7.1 Hz, CH$_3$—CH$_2$), 6.77 (1H, s, H-3).

Alternative Method for Preparing the Compounds of Formula (II)

To a mixture of ethyl propiolate (13 mmol, 1.31 ml), and of acetone redistilled over calcium sulfate (10 mmol, 0.733 ml), in solution in 50 ml of anhydrous methylene chloride, under an inert atmosphere (argon) maintained at 0° C. with stirring, a diethylaluminum iodide solution in toluene (12 mmol, 12 ml) is added over 30 minutes. The yellow solution obtained is stirred for 2 h, at 0° C. The reaction is stopped by slow addition, at 0° C. of a 2N hydrochloric acid solution.

After addition of water and decantation, the organic products are extracted with ethyl acetate (3 times 50 ml). The organic phases are washed with a saturated NaCl solution, dried over MgSO$_4$, concentrated under reduced pressure to give a yellow oil (2.04 g, 69%), whose NMR spectrum is identical to that of the compound II obtained by the first method of preparation mentioned above.

1.2. Preparation of Compounds of Formula (III): E-2-(1-hydroxy-1-methylethyl)-3-iodoprop-2-en-1-ol To a solution of ethyl Z-2-(1-hydroxy-1-methylethyl)-3-iodoacrylate (II) (4.9 mmol, 1.4 g) in anhydrous ether (30 ml), lithium aluminum hydride (2.9 mmol, 0.112 g) is added. The reaction is stirred for 1 h under an inert atmosphere (argon) at room temperature (rt). After destroying the excess lithium aluminum hydride by adding a saturated sodium sulfate solution (30 µl), the alumina precipitate is filtered. The filtrate, dried (MgSO$_4$) and evaporated under reduced pressure, gives a white residue of E-2-(1-hydroxy-1-methylethyl)-3-iodoprop-2-en-1-ol (III) (0.9 g, 75%).

$^1$H NMR: δ ppm, CDCl$_3$, 250 MHz: 1.42 (6H, s, (CH$_3$)$_2$—C), 4.44 (2H, s, CH$_2$OH), 6.48 (1H, s, H-3).

1.3. Preparation of compounds of formula (IV): Z-2-(1-hydroxy-1-methylethyl)-3-iodopropenal To a solution of E-2-(1-hydroxy-1-methylethyl)-3-iodoprop-2-en-1-ol (III) (5.7 mmol, 1.4 g) in dry methylene chloride (25 ml), manganese dioxide (10 eq., 57 mmol, 5 g) is added in portions, at room temperature (rt), under an inert atmosphere. The progress of the reaction is monitored by analytical chromatography on a silica gel plate (eluent CH$_2$Cl$_2$/MeOH 97/3). After the disappearance of the starting material, the mixture is filtered on Celite®. The filtrate, evaporated under reduced pressure, gives Z-2-(1-hydroxy-1-methylethyl)-3-iodopropenal (IV) (1.3 g, 94%) in the form of a slightly yellow oil.

ES MS M m/z 307 (M+44), 295 (M+MeOH), 263 (M+Na).

HRMS (ES+MS): calculated for C$_6$H$_9$O$_2$NaI: 262.9545; measured: 262.9545

$^1$H NMR: δ ppm, CDCl$_3$, 250 MHz: 1.43 (6H, s, (CH$_3$)$_2$—C), 7.97 (1H, s, H-3), 9.79 (1H, s, CHO).

$^{13}$C NMR: δ ppm, CDCl$_3$, 28.7 ((CH$_3$)$_2$—C), 74.2 (C—OH), 101.8 (C3-I), 149.9 (=C2), 196.8 (CHO).

IR v: 1681 cm$^{-1}$ (C=O conjugate), 1565 cm$^{-1}$ (C=C), 1369, 1282, 1176, 1085 and 963 cm$^{-1}$.

1.4. Preparation of Compounds of Formula (I): E-5-iodomethylene-6,6-dimethyl-5,6-dihydropyran-2-one

1.4.1. Purification of the Crown Ether 18-crown-6

In a 500 ml round-bottomed flask, 25 g of commercial crown ether 18-crown-6 and 63 ml of dry acetonitrile are heated and stirred until complete dissolution is obtained, protected from moisture. The mixture is allowed to cool to room temperature, and then the round-bottomed flask is immersed in an ice/acetone bath. The white crystals of the complex precipitate and are collected by filtration. These hygroscopic crystals are transferred into a 250 ml round-bottomed flask provided with a magnetic stirrer bar. The acetonitrile is evaporated under a high vacuum (0.1-0.5 Torr), at a temperature ≦40° C., for 2 to 3 h. 25 g of crown ether/CH$_3$CN are obtained.

1.4.2. Preparation of (I)

A mixture of potassium carbonate (32 mmol, 4.48 g) and crown ether 18-crown-6/CH$_3$CN (64.8 mmol, 17.1 g) in anhydrous toluene (54 ml) is stirred under an inert atmosphere, for 1 h at 25° C., and the slightly cloudy solution obtained is cooled to −20° C. The Z-2-(1-hydroxy-1-methylethyl)-3-iodopropenal (IV) (5.4 mmol, 1.3 g) and the methyl bis-trifluoroethylphosphono-acetate (5.4 mmol, 1.72 g or 1.14 ml) are added and the mixture obtained is stirred and left to warm up to 0° C. The mixture becomes creamy white. After stirring for 30 minutes at 0° C. under an inert atmosphere, an ammonium chloride solution is added to stop the reaction and the organic products are then extracted with ether. The organic phases, dried over MgSO$_4$, are evaporated under reduced pressure and give a green-yellow crystallized product (1.5 g). By chromatography on a 60H silica gel column, carried out with a heptane/ether gradient, crystallized, slightly colored E-6-dimethyl-5-iodomethylene-5,6-dihydropyran-2-one (I) is obtained (1.06 g, 74%).

ES MS m/z 287 (M+Na)

HRMS (ES+MS): calculated for $C_8H_9O_2NaI$: 286.9545; measured: 286.9530.

$^1$H NMR: δ ppm, $CDCl_3$, 250 MHz: 1.62 (6H, s, $(CH_3)_2$—C), 6.1 (1H, dd, J=10, J'=2 Hz, H-4), 6.88 (1H, d, J=2 Hz, H-9), 7.2 (1H, d, J=10 Hz, H-3), nOe between H-9 and $CH_3$.

$^{13}$C NMR: δ ppm, $CDCl_3$, 28.9 (($CH_3)_2$—C), 84.0 (C6-0), 86.4 (C9-I), 121.6 (=C4H), 142.3 ($C_3$H=), 144.9 (C5), 163.3 (C=O).

IR ν: 1695 $cm^{-1}$ (C=O conjugate), 1560, 1394, 1290, 1176, 1115, 1089 and 990 $cm^{-1}$.

EIMS: 264 M$^+$, m/z 137, 127.

UV (EtOH) γ nm: 300, log ε4.1.

EXAMPLE 2

Biological Study In Vitro of the Compounds (I) According to the Invention

The biological activity of iodomethylene-dimethyl-dihydropyranone (I), as obtained according to Example 1, was studied in vitro on five different cell lines:

KB (epidermoid carcinoma of the nasopharynx)
HCT-116 (colorectal carcinoma)
K562 (myeloid leukemia)
K562-MDR1 (myeloid leukemia; resistance to doxorubicin)
MCF7-MDR1 (mammary adenocarcinoma; resistance to doxorubicin)

The cells selected for this study were incubated at 37° C. in the presence of iodomethylene-dimethyl-dihydropyranone (I) added to the culture medium at various concentrations. All the experiments carried out made it possible to determine the degree of toxicity of the test compound, its effect on the course of the cell cycle and its capacity to induce cell death by apoptosis.

2.1. Study of Cytotoxicity

Figure 1:
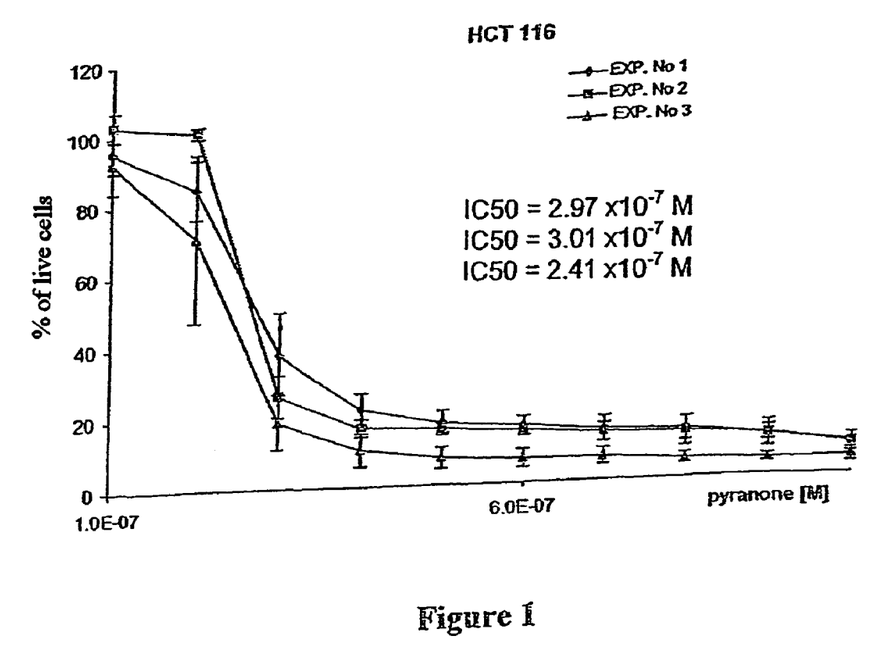
FIG. 1. Cytotoxicity of iodomethylene-dimethyl-dihydropyranone (I) on HCT-116 cells.
Figure 2:
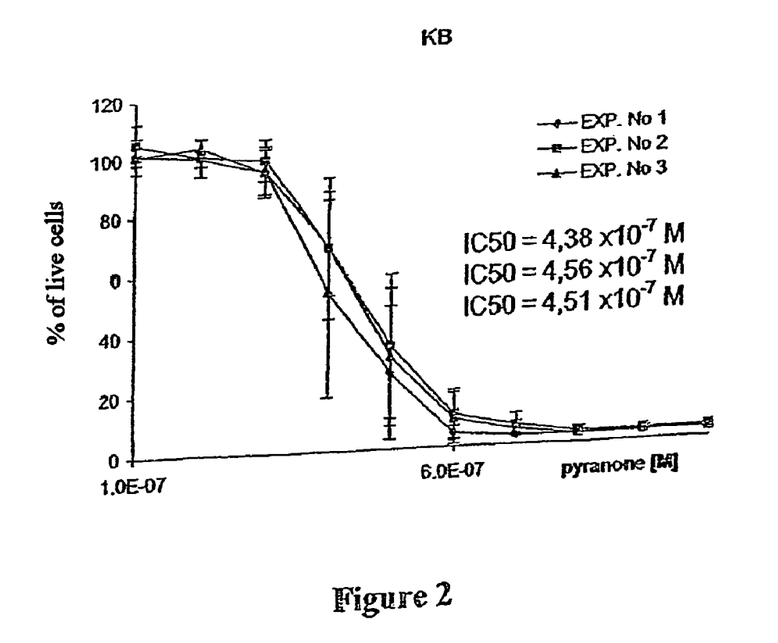
FIG. 2. Cytotoxicity of iodomethylene-dimethyl-dihydropyranone (I) on KB cells.

The cytotoxicity of iodomethylene-dimethyl-dihydropyranone (I) was evaluated on KB and HCT-116 cells. The iodomethylene-dimethyl-dihydropyranone concentration which induces the death of 50% of the cells (IC50) was determined after 96 hours of incubation and it is of the order of 0.30 micromolar for the HCT-116 cells (FIG. 1) and 0.45 micromolar for the KB cells (FIG. 2).

Figure 3:
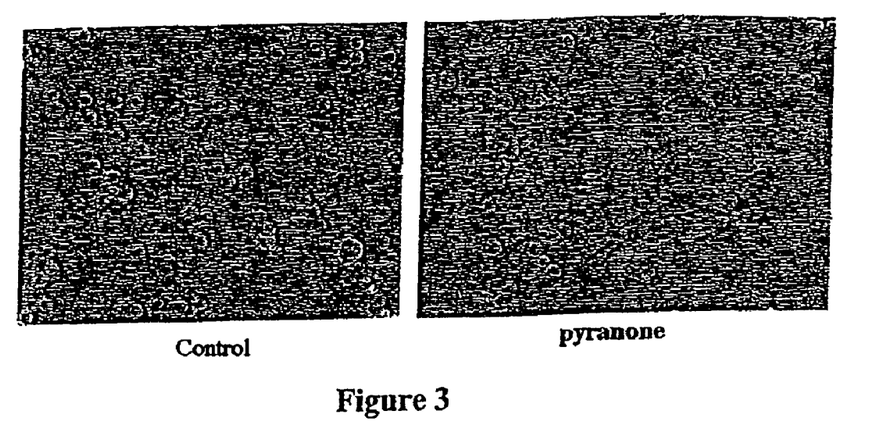
FIG. 3. Morphology of K562 cells after 24 hours treatment with control or $10^{-7}$ M of iodomethylene-dimethyl-dihydropyranone (I).

It should also be emphasized that from 24 hours onwards after the treatment with iodomethylene-dimethyl-dihydropyranone (I) at the dose of $10^{-7}$ M, a change is observed in the morphology of the treated cells. Indeed, the cells lose their round forms and become fusiform (cf. FIG. 3: treatment of K562 cells for 24 hours with compound (I) at the dose of $10^{-7}$ M).

2.2. Study of the Cell Cycle

Figure 4:
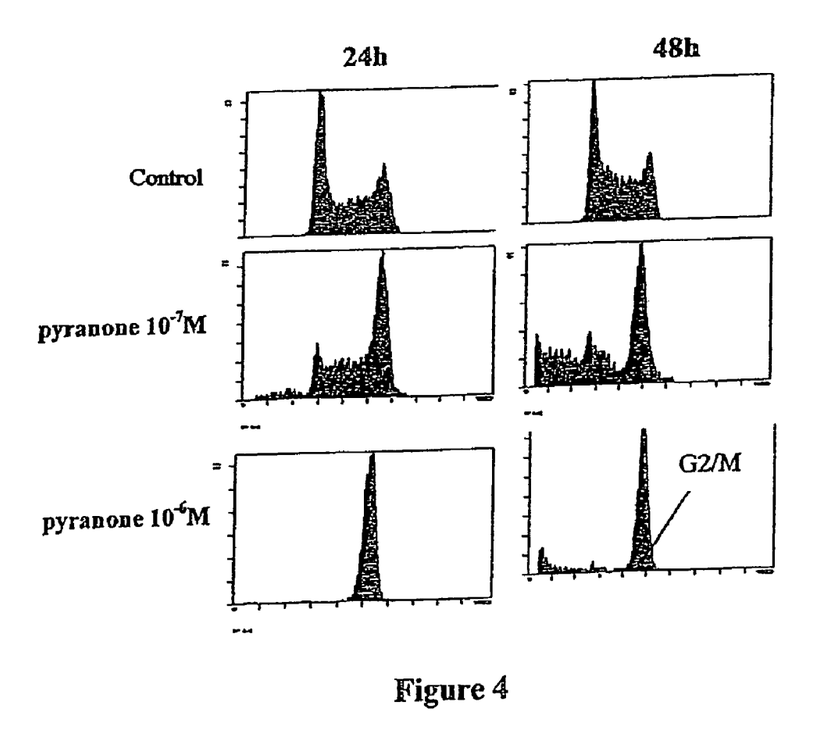
FIG. 4. Effect of control, $10^{-6}$ M or $10^{-7}$ M iodomethylene-dimethyl-dihydropyranone (I) on the cell cycle of K562 leukemia cells, as assessed by flow cytometry.

Flow cytometry analysis of the cells (K562, K562-MDR1, HCT116, MCF7-MDR1) treated with iodomethylene-dimethyl-dihydropyranone (I) showed that this compound blocks cell division in all the lines at the G2/M phase. This effect is significant after 24 hours of exposure of the cells to iodomethylene-dimethyl-dihydropyranone (I) used at the concentration $10^{-7}$ M (cf. FIG. 4: effect of (I) on the cell cycle of the leukemia cells K562).

2.3. Study of Apoptosis

Figure 5:
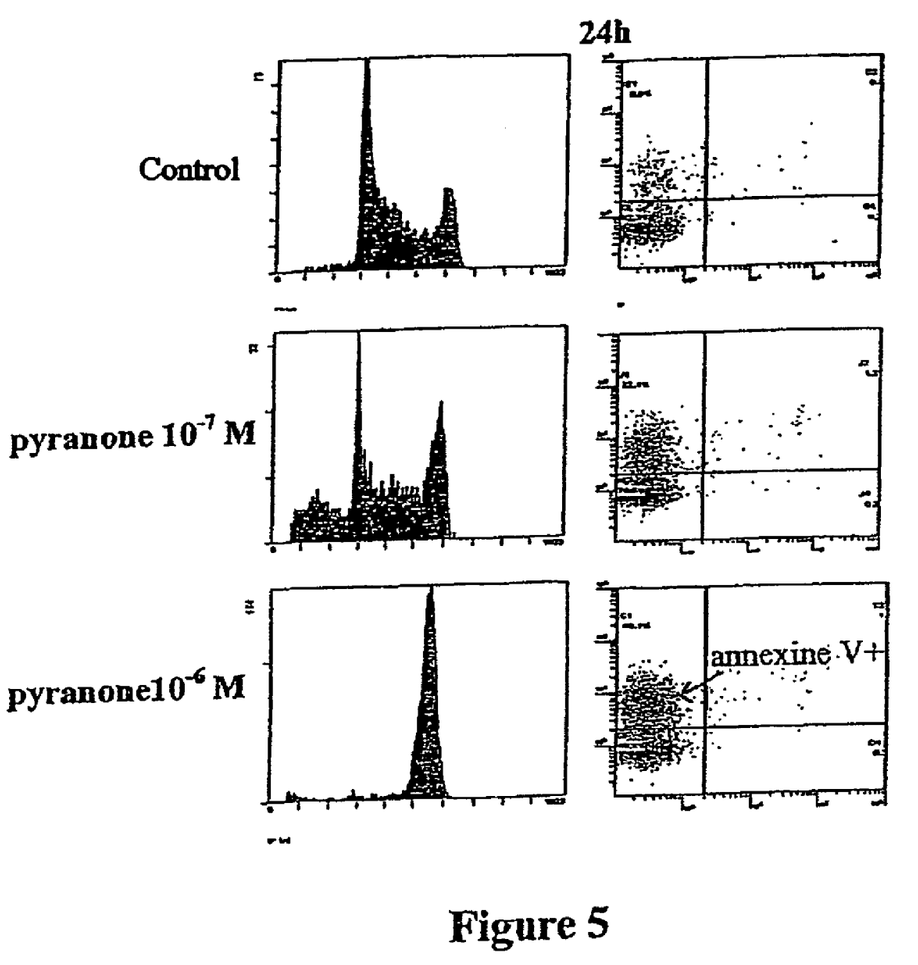
FIG. 5. Treatment of chemoresistant K562-MDR1 cells with control, $10^{-6}$ M, or $10^{-7}$ M iodomethylene-dimethyl-dihydropyranone (I) for 24 hr shows high induction of apoptosis at concentrations of $10^{-6}$ M and $10^{-7}$ M (positive annexin V/negative PI cells).

In order to specify if iodomethylene-dimethyl-dihydropyranone (I) causes cell death by apoptosis, K562 cells treated for 24 hours were analyzed by flow cytometry using double labeling: annexin V and propidium iodide (PI). The results presented in FIG. 5 show that the incubation of the (chemoresistant) K562-MDR1 cells for 24 hours with iodomethylene-dimethyl-dihydropyranone (I) at the concentrations of $10^{-6}$ M and $10^{-7}$ M leads to a high induction of apoptosis (positive annexin V/negative PI cells).

EXAMPLE 3

Biological Study In Vivo of the Compounds (I) According to the Invention 3.1. Determination of the Maximum Tolerated Dose of iodomethylene-dimethyl-dihydropyranone (I) for a Single Injection (Maximum Tolerated Dose for a Single Injection) and for Four Repeated Injections (Maximum Tolerated Dose for Four Injections)

The iodomethylene-dimethyl-dihydropyranone (I), as obtained according to Example 1, was injected by the intravenous route (iv) to 4-5 week old Nude mice (Swiss Nu/nu) at the following doses: 50 mg/kg, 66.6 mg/kg, 100 mg/kg, 150 mg/kg and 200 mg/kg. The monitoring of the survival of the animals, and their weight, up to day 21 revealed a toxicity for the doses of 150 and 200 mg/kg, which puts the maximum tolerated dose for a single injection at 100 mg/kg.

Having determined the maximum tolerated dose for a single injection, the Nude mice were treated by the intravenous (iv) route with iodomethylene-dimethyl-dihydropyranone (I) injected at three different doses: 50, 70 and 90 mg/kg/injection. Each dose was administered 4 times at 3 day intervals (D0, D3, D6 and D9). The survival of the animals, their weight and clinical signs noted up to day 21 made it possible to establish the value of the maximum tolerated dose for four injections which is at less than 90 mg/kg. The 40, 60 and 80 mg/kg doses were therefore chosen for the evaluation of antitumor activity.

3.2. Evaluation of the Antitumor Activity of iodomethylene-dimethyl-dihydropyranone (I) Administered by the Intravenous Route in Nude Mice Carrying a Transplanted Tumor HCT 116

The xenotransplantation of human tumor cells in Nude mice is a model commonly used for the evaluation of the antitumor activity of various molecules.

Nude mice carrying an HCT 116 tumor transplanted under the skin were treated with iodomethylene-dimethyl-dihydropyranone (I) administered by the intravenous (iv) route at three different doses (40, 60 and 80 mg/kg/injection), chosen according to the tolerance to this compound demonstrated in the preceding study. The iodomethylene-dimethyl-dihydropyranone (I) was injected 4 times at 3 day intervals (D0, D3, D6 and D9). Two groups of control animals were formed. The first group received no injection (control), whereas the animals of the second group received injections of the solution which served to solubilize the iodomethylene-dimethyl-dihydropyranone (I) (vehicle).

The volume of the tumors (mm$^3$) was measured with a caliper twice per week. The tumor growth curves (FIG. 6A) show that from the 2nd injection, iodomethylene-dimethyl-dihydropyranone (I) at the dose of 80 mg/kg/injection significantly inhibits the tumor progression.

Based on one of the parameters for evaluating the inhibition of tumor growth which is the percentage T/C [T/C= (median of the volume of the tumors in the treated group/median of the volume of the tumors in the control group)× 100] which reaches 53.5% 21 days after the start of the treatments, iodomethylene-dimethyl-dihydropyranone (I) has an antitumor activity close to that observed with the effective antitumor drugs according to the NIH standards (T/C≦42%).

Figure 6:
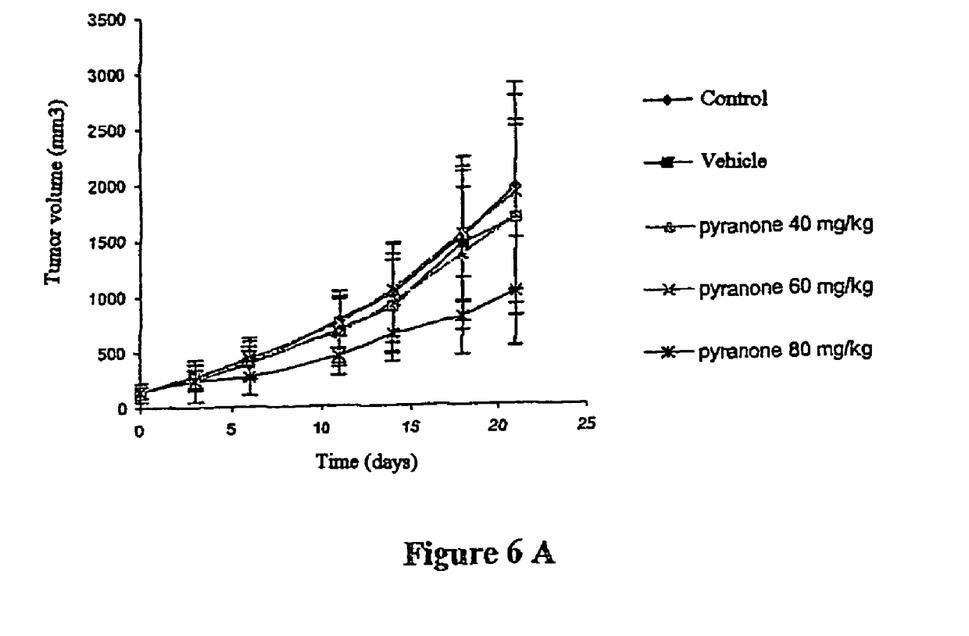
FIG. 6A. Volume (mm 3) of HCT116 tumor in Nude mice treated with control, vehicle, or intravenous iodomethylene-dimethyl dihydropyranone (I) route at three different doses (40, 60 and 80 mg/kg/injection).
FIG. 6B. Nude mice containing tumors showed no weight difference after treatment with control, vehicle, or intravenous iodomethylene-dimethyl-dihydropyranone (I) route at three different doses (40, 60 and 80 mg/kg/injection), indicating an absence of acute toxicity.

The data presented in FIG. 6B show the absence of acute toxicity of iodomethylene-dimethyl-dihydropyranone (I) which results in normal growth of the mice. Indeed, the body weight of the treated mice increases uniformly up to the end of the treatment.

The invention claimed is:

1. A compound corresponding to formula (I):

I in which

X represents chlorine, bromine or iodine, and $R_1$ and $R_2$ represent, each independently of the other, a hydrogen atom, an alkyl, cycloalkyl or alkylene group, which is linear or branched, containing from 1 to 6 carbon atoms, $R_1$ and $R_2$ form together a 5-, 6-, 7- or 8-membered ring, including its isomers, its enantiomers, its diastereoisomers, and mixtures thereof.

2. The compound of formula (I) as claimed in claim 1, wherein X represents chlorine, bromine or iodine, and $R_1$ and $R_2$ represent, each independently of the other, a hydrogen atom, an alkyl or alkylene group, which is linear or branched, containing from 1 to 6 carbon atoms, or $R_1$ and $R_2$ form together a 5-, 6-, 7- or 8-membered ring.

3. The compound of formula (I) as claimed in claim 1, wherein X represents iodine.

4. The compound of formula (I) as claimed in claim 1, wherein $R_1$ and $R_2$ each represent independently of each other a hydrogen atom, a methyl, ethyl, propyl or butyl group.

5. The compound of formula (I) as claimed in claim 1, wherein $R_1$ and $R_2$ each represent a methyl group.

6. The compound of formula (I) as claimed in claim 1, wherein it is iodomethylene-dimethyl-dihydropyranone.

7. The compound of formula (I) as claimed in claim 1, wherein it is the isomer E-iodomethylene-dimethyl-dihydropyranone.

8. A method for preparing a compound of formula (I) as claimed in claim 1, wherein a Homer-Emmons reaction is carried out by reacting an aldehyde of formula (IV)

IV in which the meanings of X, $R_1$ and $R_2$ are those defined for the compound of formula (I) as claimed in claim 1, with a phosphonate such as methyl [bis(2,2,2-trifluoroethyl)phosphinoyl]acetate, followed by cyclization.

9. The method as claimed in claim 8, wherein the preparation of the compound of formula (I) is carried out in the presence of a base such as potassium carbonate and a crown ether such as the crown ether 18-crown-6.

10. The method as claimed in claim 8, wherein the preparation of the compound of formula (I) from the compound of formula (IV) is preceded by the following steps:
   i) a compound of formula (II) is first of all reacted with a reducing agent such as lithium aluminum hydride, resulting in the formation of the corresponding primary alcohol (III), and then
   ii) the compound of formula (III) is reacted with an oxidizing agent such as manganese dioxide to give the corresponding aldehyde (IV)

in which

X represents chlorine, bromine or iodine, and $R_1$ and $R_2$ represent, each independently of the other, a hydrogen atom, an alkyl, cycloalkyl or alkylene group, which is linear or branched, containing from 1 to 6 carbon atoms, or $R_1$ and $R_2$ form together a 5-, 6-, 7- or 8-membered ring, and R represents a linear alkyl group containing from 1 to 5 carbon atoms, such as a methyl or ethyl group.

11. A compound corresponding to formula (IV):

IV in which the meanings of X, $R_1$ and $R_2$ are those defined for the compound of formula (I) as claimed in claim 1, including its isomers, its enantiomers, its diastereoisomers, and mixtures thereof.

12. A medicament consisting of a compound of formula (I) as claimed in claim 1.

13. A pharmaceutical composition comprising a compound of formula (I) as claimed in claim 1, in combination with any appropriate excipient.

14. The composition as claimed in claim 13, wherein it is intended to be administered by intravenous injection.

15. A method for treating cancer in a patient comprising administering to said patient the compound according to claim 1.

* * * * *

UNITED STATES PATENT AND TRADEMARK OFFICE
CERTIFICATE OF CORRECTION

| | |
|---|---|
| PATENT NO. | : 7,405,309 B2 |
| APPLICATION NO. | : 10/585974 |
| DATED | : July 29, 2008 |
| INVENTOR(S) | : Joanna Bakala et al. |

Page 1 of 1

It is certified that error appears in the above-identified patent and that said Letters Patent is hereby corrected as shown below:

Column 2, line 32, please delete: "FIG. 4. Effect of control, $10^{-6}$ M" and replace with -- FIG. 4. Effect of $10^{-6}$ M -- .

Column 2, line 36, please delete: "with control, $10^{-6}$ M," and replace with -- with $10^{-6}$ M --.

Column 2, line 41, please delete: "treated with control, vehicle," and replace with -- treated with vehicle --.

Column 2, line 45, please delete: "difference after treatment with control, vehicle," and replace with -- difference after treatment with vehicle -- .

In Column 13, Claim 8, line 53, please delete: "wherein a Homer-Emmons reaction" and replace with -- wherein a Horner-Emmons reaction --.

Signed and Sealed this

Seventh Day of April, 2009

JOHN DOLL
*Acting Director of the United States Patent and Trademark Office*